(12) United States Patent
Miki et al.

(10) Patent No.: US 9,445,710 B2
(45) Date of Patent: Sep. 20, 2016

(54) PUMP UNIT AND ENDOSCOPE APPARATUS USING THE SAME

(71) Applicants: KEIO UNIVERSITY, Tokyo (JP); OLYMPUS CORPORATION, Tokyo (JP)

(72) Inventors: Norihisa Miki, Yokohama (JP); Yoshiyuki Okayama, Yokohama (JP); Keijiro Nakahara, Yokohama (JP); Kaori Yoshimura, Yokohama (JP); Shinji Yasunaga, Higashimurayama (JP)

(73) Assignees: OLYMPUS CORPORATION, Tokyo (JP); KEIO UNIVERSITY, Tokyo (JP)

( * ) Notice: Subject to any disclaimer, the term of this patent is extended or adjusted under 35 U.S.C. 154(b) by 533 days.

(21) Appl. No.: 13/785,323

(22) Filed: Mar. 5, 2013

(65) Prior Publication Data

US 2013/0184522 A1 Jul. 18, 2013

Related U.S. Application Data

(63) Continuation of application No. PCT/JP2011/072256, filed on Sep. 28, 2011.

(30) Foreign Application Priority Data

Oct. 6, 2010 (JP) .................... 2010-226865

(51) Int. Cl.
*F04B 43/04* (2006.01)
*A61B 1/00* (2006.01)
*A61B 1/12* (2006.01)
*F04B 43/02* (2006.01)

(52) U.S. Cl.
CPC .......... *A61B 1/00131* (2013.01); *A61B 1/128* (2013.01); *F04B 43/025* (2013.01); *F04B 43/046* (2013.01); *A61B 1/0008* (2013.01)

(58) Field of Classification Search
CPC .......................... F04B 43/046; F04B 43/025
USPC ............................... 417/375, 413.2
See application file for complete search history.

(56) References Cited

U.S. PATENT DOCUMENTS

2009/0129952 A1* 5/2009 Patrascu et al. ............. 417/322
2009/0253957 A1 10/2009 Yasunaga

FOREIGN PATENT DOCUMENTS

JP 07-027056 A 1/1995
JP 2003-286958 A 10/2003
(Continued)

OTHER PUBLICATIONS

International Search Report dated Dec. 20, 2011 issued in PCT/JP2011/072256.
(Continued)

*Primary Examiner* — Patrick Hamo
(74) *Attorney, Agent, or Firm* — Scully, Scott, Murphy & Presser, P.C.

(57) ABSTRACT

A pump unit which can be made to be small-sized, and which enables to achieve a sufficient flow and an endoscope apparatus using such pump are provided. The pump unit which transports a fluid in a channel upon generating a progressive wave which is propagated in a longitudinal direction of the channel, in a first flexible thin film which constitutes at least a part of a channel-wall surface, includes a vibration exciter unit.

15 Claims, 11 Drawing Sheets

(56) References Cited

FOREIGN PATENT DOCUMENTS

| | | |
|---|---|---|
| JP | 2005-069052 A | 3/2005 |
| JP | 2005-188418 A | 7/2005 |
| JP | 2007-298010 A | 11/2007 |
| JP | 2009247560 A | 10/2009 |
| JP | 2010-167106 A | 8/2010 |

OTHER PUBLICATIONS

Suzuki, Takaaki et al., "Development of Valveless Micropump Piezoelectrically Driven by Traveling Wave", Journal of JSAEM (2005), vol. 13, No. 4, pp. 310-315.

Suzuki, Takaaki et al., "Improving the Performance of a Traveling Wave Micropump for Fluid Transport in Micro Total Analysis Systems", Complex Medical Engineering (2007), pp. 3-12.

* cited by examiner

100

100

100

PUMP UNIT AND ENDOSCOPE APPARATUS USING THE SAME

CROSS-REFERENCE TO RELATED APPLICATIONS

The present application is based upon and claims the benefit of priority from prior Japanese Patent Application No. 2010-226865 filed on Oct. 6, 2010; the entire contents of which is incorporated herein by reference.

TECHNICAL FIELD

The present invention relates to a pump unit and an endoscope apparatus using the same.

BACKGROUND ART

A method of sending a liquid by a peristaltic movement which occurs at an interface with a liquid inside a channel by generating a progressive wave in a flexible member which constitutes at least a part of a wall surface of the channel has been proposed (Patent Document 1, Non-patent Document 1). In a pump unit in which, the abovementioned method has been used, a complicated mechanism such as a chuck valve is unnecessary, and therefore it is suitable for small-sizing. When a small-size pump unit is realized, by disposing the small-size pump unit at a front-end portion of an endoscope, it is possible to realize a simple and highly reliable cooling mechanism which circulates a cooling medium in a closed-loop channel which is extended rearward from the front-end portion of the endoscope.

CITATION LIST

Patent Literature

Patent Document 1: Japanese Patent Application Laid-open Publication No. 2003-286958

Non Patent Literature

Non-patent Document 1: Pages 310~315 of No. 4 (2005), Volume 13 of 'Journal of the Japan Society of Applied Electromagnetics and Mechanics (JSAEM)'

SUMMARY OF THE INVENTION

Technical Problem

For installing a pump unit in a front-end portion of an endoscope apparatus, a cross-sectional area is desired to be made small up to an extent of few $mm^2$, and small-sizing to such level in the abovementioned conventional pump has been difficult.

A problematic point in the pump unit described in Patent Document 1 is that a plurality of actuators for generating a progressive wave is necessary. The need of the plurality of actuators hinders the small-sizing and cost reduction of the pump unit, and also necessitates a large number of wires for drive. Running the large number of wires through a shaft portion of the endoscope in particular, is difficult due to a constraint on space.

In the pump unit described in Non-patent Document 1, for achieving sufficient flow, it is necessary to generate a progressive wave having large amplitude, and simply assembling a vibration exciter mechanism of a large displacement leads to an increase in size of the pump unit.

The present invention has been made in view of the abovementioned issues, and an object of the present invention is to provide a pump unit which can be made to be small-sized, and which enables to achieve a sufficient flow, and an endoscope apparatus using such pump unit.

Solution to Problem

To solve the abovementioned issues and to achieve the object, a pump unit according to a first aspect of the present invention, which transports a fluid in a channel by generating a progressive wave which is propagated in a longitudinal direction of the channel, in a first flexible thin film which constitutes at least a part of a channel-wall surface, includes a vibration exciter unit which generates a progressive wave by exciting by vibrations a predetermined part of the first flexible thin film in an out-of-plane direction.

A pump unit according to a second aspect of the present invention transports a fluid in a channel by generating a progressive wave which is propagated in a longitudinal direction of the channel, in a first flexible thin film which constitutes at least a part of a channel-wall surface, and the first flexible film constitutes a part of a chamber in which, an incompressible fluid is enclosed, and a second flexible thin film constitutes another part of the chamber, and a progressive wave is generated in the second flexible thin film by a vibration exciter mechanism which acts on the second flexible thin film and a progressive wave is generated in the first flexible thin film by a displacement of the incompressible fluid due to the progressive wave which has been generated in the second flexible thin film, and an out-of-plane displacement of the progressive wave generated in the first flexible thin film is practically larger than an out-of-plane displacement of the progressive wave generated in the second flexible thin film In the pump unit according to the second aspect of the present invention, it is preferable that the vibration exciter mechanism which acts on the second flexible thin film generates a progressive wave by exciting by vibrations a predetermined part of the second flexible thin film in an out-of-plane direction.

In the pump unit according to the second aspect of the present invention, it is preferable that the chamber has a structure which is formed by the first flexible thin film and the second flexible thin film facing mutually, on both principal surfaces of a plate member having an opening (aperture).

Furthermore, it is preferable that a plate member or a thin film member having an opening smaller than the opening in the plate member is stacked on the first flexible thin film.

An endoscope apparatus according to the present invention includes a cooling mechanism, and in the endoscope apparatus including the cooling mechanism, the abovementioned pump unit is disposed in a part of a circulation channel which is extended in a longitudinal direction of an endoscope from a front-end portion at which, an electronic equipment is disposed.

Advatangeous Effects of Invention

The pump unit and the endoscope apparatus according to the present invention show an effect that small-sizing is possible, and it is possible to achieve sufficient flow.

DESCRIPTION OF EMBODIMENTS

Exemplary embodiments of a pump unit and an endoscope apparatus using the same according to the present invention will be described below in detail by referring to the accompanying diagrams. However, the present invention is not restricted to the embodiments described below.

The pump unit according to the present invention, to start with, generates a progressive wave by causing an out-of-plane displacement of an end portion of a flexible thin film. Accordingly, it is possible to operate a pump (the pump unit) by a single actuator.

Furthermore, the pump unit according to the present invention includes an out-of-plane displacement augmentation mechanism by a chamber in which, an incompressible fluid is enclosed between a vibration exciter mechanism and a channel. Accordingly, sufficient flow of a liquid to be transported is achieved even by a vibration exciter mechanism with a small displacement.

First Embodiment (Structure of Micro Pump)

A structure of a micro pump as a pump unit according to a first embodiment will be described below.

Figure 1:
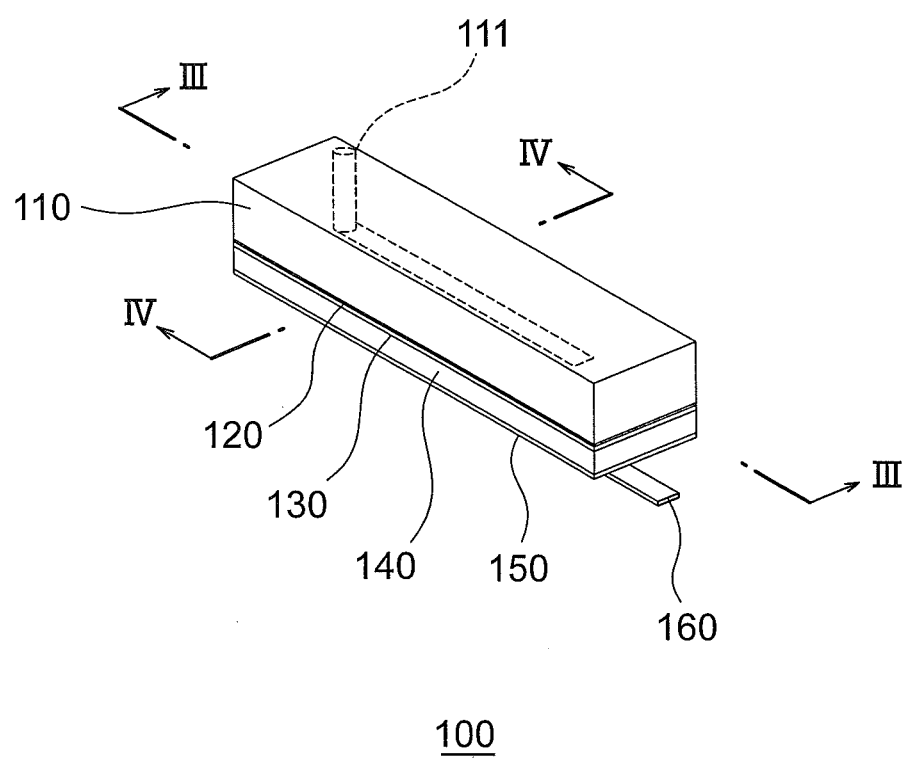
FIG. 1 is a perspective view showing a state in which, a micro pump according to a first embodiment is installed.
Figure 2:
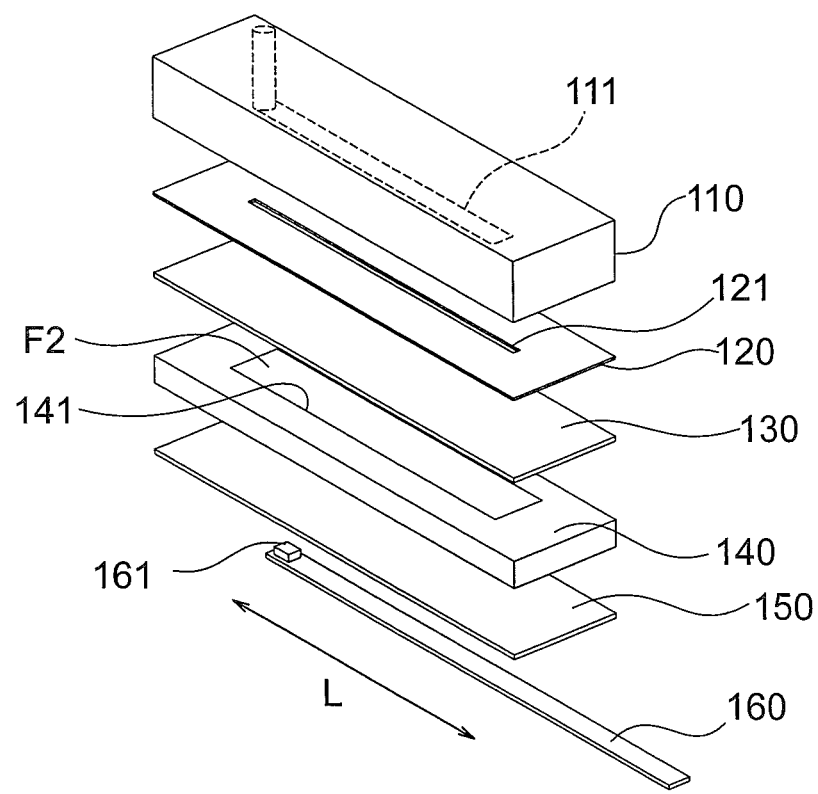
FIG. 2 is an exploded perspective view showing a structure of the micro pump according to the first embodiment.
Figure 3:
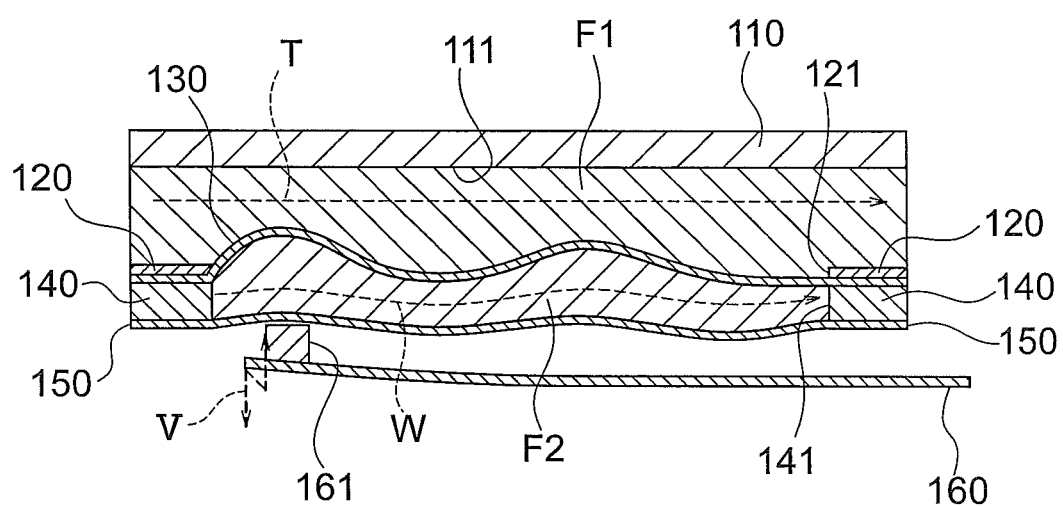
FIG. 3 is a cross-sectional view along a line in FIG. 1, showing schematically a state when the micro pump is in operation.
Figure 4:
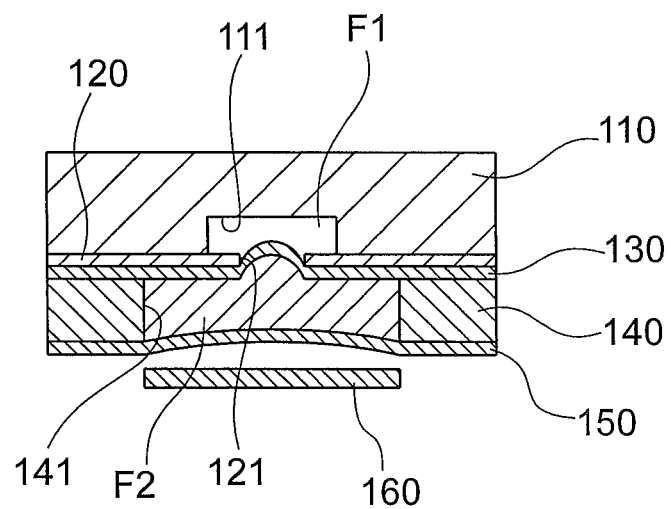
FIG. 4 is a cross-sectional view along a line IV-IV in FIG. 1, showing an internal structure of the micro pump.

FIG. 1 is a perspective view showing a state in which, a micro pump 100 according to the first embodiment is assembled. FIG. 2 is an exploded perspective view showing a structure of the micro pump 100. FIG. 3 is a cross-sectional view along a line in FIG. 1, showing schematically a state when the micro pump 100 is in operation. FIG. 4 is a cross-sectional view along a line IV-IV in FIG. 1, showing an internal structure of the micro pump 100. Here, FIG. 3 is a cross-sectional view along a longitudinal direction including a channel 111 of the micro pump 100.

As shown in FIG. 2 to FIG. 4, the micro pump 100 has a structure in which, a PDMS fluid channel 110 in which, the channel 111 is formed, a titanium cover 120 which includes an opening (aperture) portion 121 at a position corresponding to (facing) the channel 111, a first PDMS film 130 as a first flexible thin film, a silicon substrate 140 in which, a chamber 141 is formed at a position corresponding to the opening portion 121 in the titanium cover 120, a second PDMS film 150 as a second flexible thin film, and an actuator 160 are stacked in order from an upper side in a direction of height. Each of the PDMS fluid channel 110, the titanium cover 120, the first PDMS film 130, the silicon substrate 140, the second PDMS film 150 has a substantially same rectangular flat shape with a direction in which the channel 111 is extended as a longitudinal direction (L-direction in FIG. 2). Here, PDMS is polydimethylsiloxane.

As shown in FIG. 4, the channel 111 constitutes an inner wall of the opening portion 121 which is cut through a direction of thickness of the titanium cover 120, and a lower portion by the first PDMS film 130. Consequently, the channel 111 is formed by an inner wall of the PDMS fluid channel 110, the inner wall of the opening portion 121, and the first PDMS film 130. A fluid F1 which is to be transported is accommodated in the channel 111.

As shown in FIG. 4, the chamber 141 is cut through a direction of thickness of the silicon substrate 140, and has a structure in which, an upper surface thereof is covered by the first PDMS film 130, and a lower surface thereof is covered by the second PDMS film 150. Consequently, the chamber 141 is formed by the first PDMS film 130, an inner wall of the silicon substrate 140, and the second PDMS film 150. An incompressible fluid F2 is filled in the chamber 141.

As shown in FIG. 2 and FIG. 3, a contact-pressure member 161 which is displaced by the actuator 160 of a piezoelectric type which is curved, is disposed to be in contact on a lower surface of the second PDMS film 150. The contact-pressure member 161 is fixed to a front-end upper surface of the actuator 160 in the form of a long plate, as well as is disposed at a position on one end portion in a longitudinal direction of the chamber 141, corresponding to (facing) the channel 111. In the micro pump 100, the actuator 160 and the contact-pressure member 161 form the vibration exciter mechanism. Moreover, the titanium cover 120, the first PDMS film 130, the silicon substrate 140, the second PDMS film 150, and the incompressible fluid F2 in the chamber 141 form the vibration exciter unit.

The contact-pressure member 161 excites by vibrations (vibration V in FIG. 3) an end portion of the second PDMS film 150 in an out-of-plane direction. Due to the vibration excitation, a progressive wave toward a direction in which the channel 111 is extended is generated in the second PDMS film 150. Since the incompressible fluid F2 is filled in the chamber 141, due to the progressive wave generated in the second PDMS film 150, a corresponding progressive wave is generated also in the first PDMS film 130. Consequently, the incompressible fluid F2 is transported inside the chamber 141 in a W-direction in FIG. 3, and the fluid F1 inside the channel 111 is transported in a T-direction in FIG. 3.

Here, the out-of-plane direction is a direction other than an in-plane direction (left-right direction in FIG. 3 and FIG. 4) of the second PDMS film 150 in the form of a plate before being excited by vibration, and in other words, is a direction other than an in-plane direction on an upper surface and a lower surface of the titanium cover 120. The out-of-plane direction includes at least a direction perpendicular to a surface of the second PDMS film 150 before being excited by vibration, and in other words, includes a direction of height of the micro pump 100 (vertical direction in FIG. 1 to FIG. 4).

Moreover, both the opening portion 121 formed in the titanium cover 120 and the chamber 141 formed in the silicon substrate 140 are through openings having a rectangular shape which is longer in a direction of the channel 111. The opening portion 121 in the titanium cover 120 has a width narrower than the chamber 141 in the silicon substrate 140. Since a stiffness of the titanium cover 120 is higher than a stiffness of the first PDMS film 130, a displacement of the first PDMS film 130 is suppressed in a portion fixed to the titanium cover 120, and the displacement of the first PDMS film 130 occurs in a range corresponding to the opening portion 121 in the titanium cover 120. In other words, from a view point of the range of displacement, practically, the range in which the displacement occurs in the first PDMS film 130 on an upper side becomes smaller than a range in which, the displacement occurs in the second PDMS film 150 on a lower side.

In such manner, a displaceable range by the titanium cover 120 for the first PDMS film 130 on the upper side is formed to be practically smaller as compared to a displaceable range by the titanium cover 120 for the second PDMS 150 on the lower side. Therefore, the displacement in the out-of-plane direction of the first PDMS film 130 on the upper side is restricted to the range corresponding to the opening portion 121, and an amount of displacement becomes larger than the amount of displacement of the second PDMS film 150 on the lower side. In other words, by making the opening portion 121 smaller than the chamber 141, an effect of augmentation of the displacement in the out-of-plane direction in (for) the first PDMS film 130 is achieved. Consequently, it is possible to transport a liquid by a single actuator for vibration excitation and also a large flow of a liquid to be transported is achieved by a small displacement of the actuator for vibration excitation.

Here, as a method of manufacturing, in FIG. 2, since it is possible to fabricate members except the actuator 160 and the PDMS fluid channel 110 by a batch processing of MEMS (micro electro mechanical system) process in which, a silicon wafer is used, the cost-reduction is possible.

Instead of an arrangement of providing the titanium cover 120 as mentioned above, it is possible to achieve a similar effect also by thinning locally a region of an area similar to the opening portion 121 of the titanium cover 120 in a PDMS film equivalent to the first the first PDMS film 130. In other words, since a portion of the PDMS film which has been thinned is susceptible to be displaced more than a portion of the PDMS film which has not been thinned, a displacement of the progressive wave which has been generated in the second PDMS film 150 and transmitted via the incompressible fluid F2 is augmented.

Example of Application to Cooling Mechanism of Endoscope

Figure 5:
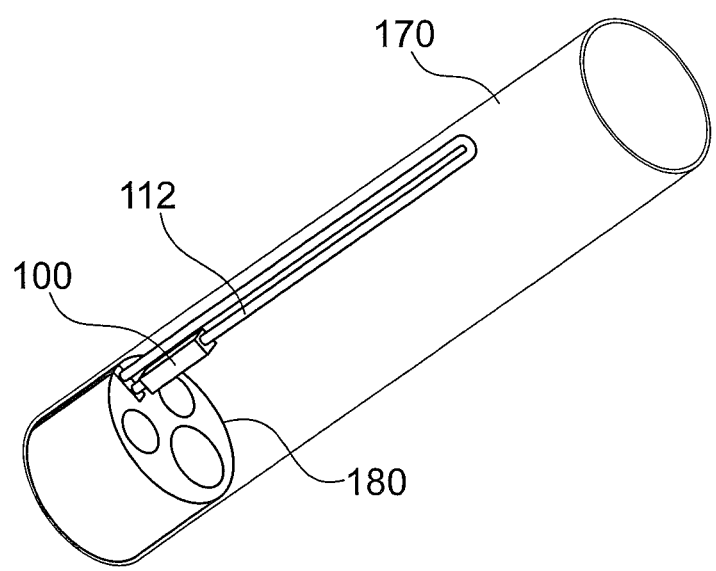
FIG. 5 is a perspective view showing a schematic structure when the micro pump according to the first embodiment is applied to an endoscope apparatus.
Figure 6:
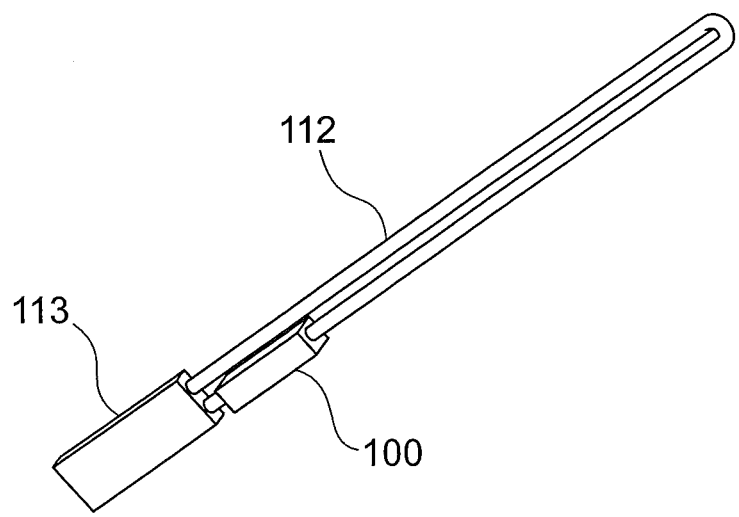
FIG. 6 is a perspective view showing a structure of a water-cooling unit according to the first embodiment.

An example in which, the micro pump 100 shown in diagrams from FIG. 1 to FIG. 4 is applied to an endoscope apparatus will be described below. FIG. 5 is a perspective view showing a schematic structure when the micro pump 100 according to the first embodiment is applied to the endoscope apparatus. FIG. 6 is a perspective view showing a structure of a water-cooling unit according to the first embodiment.

A commonly used endoscope has a shape of a long and thin tube, and functional elements such as an image pickup unit and a light source are disposed at a front-end portion thereof. With an achievement of high functionality of endoscopes in recent years, a heat generation of the functional elements at the front-end portion has been becoming problematic. Therefore, development of a liquid-cooling unit which cools down the front-end portion effectively has been sought, and practically disposing a liquid transporting pump at the front-end portion which generates heat is difficult from a point of space, and an actual situation has been such that there is no other way than disposing the pump at a location away from the front-end portion, such as an operating section of the endoscope or at an exterior of the endoscope.

In the example shown in FIG. 5, at the front-end portion of the endoscope apparatus, a water-cooling unit including the micro pump 100 is assembled in an outer peripheral portion of a metallic member 180 on which various functional elements (omitted in the diagram) are assembled.

FIG. 6 shows only the water-cooling unit shown in FIG. 5. The water-cooling unit includes a water-cooling jacket 113 made of a metallic material, which is provided with a channel at an interior, a tube 112 which is connected to the channel inside the water-cooling jacket 113, and which circulates a cooling-liquid, and the micro pump 100 which is disposed at some mid-point of the tube 112. The tube 112 and the channel inside the water-cooling jacket 113 form a closed loop of the cooling liquid. The cooling liquid in the tube 112 is circulated inside the closed loop by using the micro pump 100. The tube 112 is disposed inside a casing 170 (such as a curved tube or a corrugated tube) of the endoscope, to be extended in a direction in which, the casing 170 is extended (longitudinal direction of the endoscope).

The water-cooling jacket 113 is assembled on the metallic member 180 at the front-end portion, and a heat-transfer is carried out between the water-cooling jacket 113 and the metallic member 180. Moreover, the heat which has moved from the water-cooling jacket 113 to the cooling liquid is discharged to a surrounding area at a rear side of the endoscope in a process of flowing inside the tube 112. By discharging the cooling liquid to the surrounding area repeatedly, it is possible to lower a temperature of the metallic member 180.

As it has been mentioned above, the micro pump 100 is capable of achieving a large flow with a small size, and also has a long and thin shape. Therefore, the micro pump 100 is favorable particularly for an endoscope which has a strict constraint of space in a radial direction (direction perpendicular to the longitudinal direction). Moreover, since the micro pump 100 functions with a single actuator 160 of piezoelectric type as mentioned above, a fact that the number of wires required is small is also advantageous from a viewpoint of reliability and improvement of assembly work.

Furthermore, in the water-cooling unit in which the micro pump 100 is used, a short tube for circulating the cooling liquid serves the purpose. In other words, in a case of disposing the conventional pump at the operating section, it is necessary to draw the tube for transporting a liquid up to the front-end portion, whereas, in the water cooling unit in which the micro pump 100 is used, although it depends on an amount of heat generated by the front-end portion, it is possible to achieve sufficient cooling effect even without drawing around the tube 112 from the front-end portion up to the operating section. Consequently, by using the micro pump 100, it is possible to improve reliability with a simple structure than in a conventional type in which a cooling-liquid circulation tube is drawn up to the operating section of the endoscope or up to the exterior of the endoscope.

Second Embodiment

Figure 7:
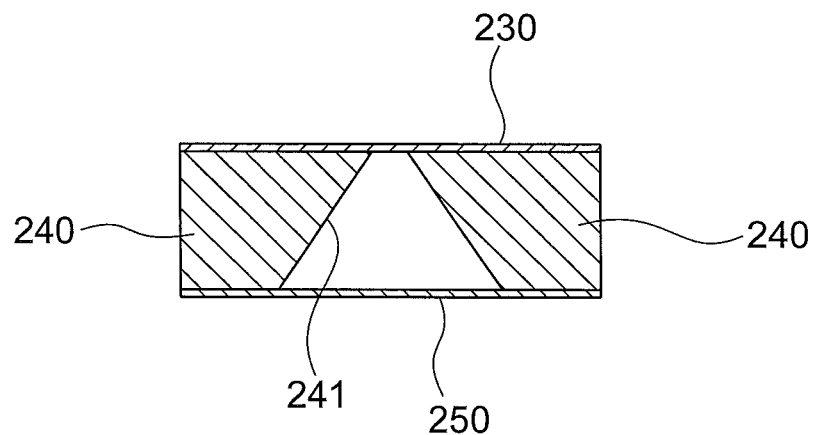
FIG. 7 is a cross-sectional view along a vertical direction, showing a structure of a micro pump according to a second embodiment.
Figure 8:
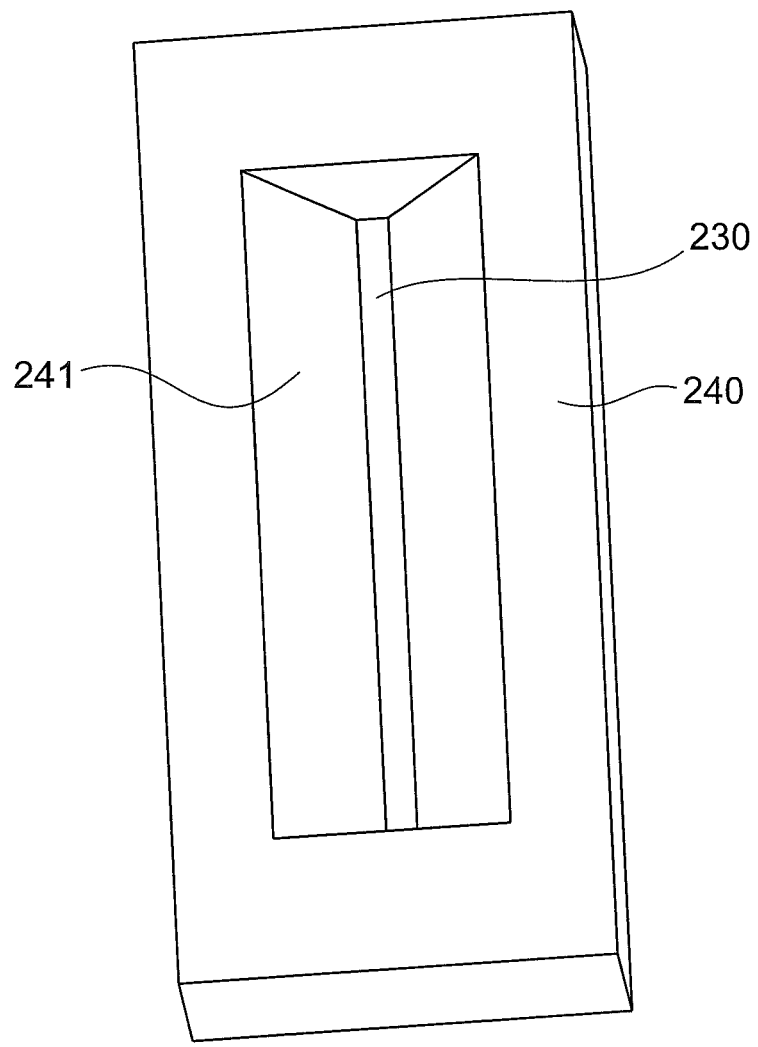
FIG. 8 is a perspective view showing a structure of the micro pump according to the second embodiment, when viewed from a second PDMS film side.

FIG. 7 is a cross-sectional view along a vertical direction, showing a structure of a micro pump 200 according to a second embodiment. FIG. 8 is a perspective view showing a structure of the micro pump 200, when viewed from a second PDMS film 250 side. In FIG. 7, members corresponding to the PDMS fluid channel 110 and the actuator 160 in the first embodiment are not shown. Moreover, in FIG. 8, the second PDMS film 250 is not shown in the diagram.

In the micro pump 100 according to the first embodiment, for making a deformation area of the first PDMS film 130 on the upper side smaller than a deformation area of the second PDMS film 150, a titanium cover 120 which suppresses a deformation of the first PDMS film 130 has been formed. Whereas, in the micro pump 200 according to the second embodiment, for making a deformation area of a first PDMS film 230 (first flexible thin film) on an upper side smaller than (a deformation area of) the second PDMS film 250 (second flexible thin film) on a lower side, a size of a chamber 241 of a silicon substrate 240 has been changed. Concretely, the chamber 242 is formed such that the size of the chamber 241 in an orthogonal cross-section in a vertical direction (vertical direction in FIG. 7) of the silicon substrate 240 becomes smaller gradually from the second PDMS film 250 toward the silicon substrate 240. The incompressible liquid F2 is enclosed in the chamber 241.

Fabrication of the chamber 241 of the silicon substrate 240 of which, a cross-section assumes such trapezoidal shape can be carried out comparatively easily by using an anisotropic etching by a strong alkali solution, upon selecting an appropriate plane direction.

A PDMS fluid channel is stacked on the first PDMS film 230 similarly as the PDMS fluid channel 110 in the first embodiment, and an actuator of a piezoelectric type is disposed to be in contact on a lower surface of the second PDMS film 250 similarly as the actuator 160 in the first embodiment.

In such a structure, a displacement of the second PDMS film 250 and the first PDMS film 230 occurs in a range corresponding to the chamber 241. Consequently, a range in which the displacement of the first PDMS film 230 occurs is smaller than a range in which the displacement of the second PDMS film 250 occurs. Therefore, by changing a width of a deformation area of the first PDMS film 230 on the upper side and the second PDMS film 250 on the lower side without using a titanium cover, a displacement augmentation effect similar as in the first embodiment is achieved.

Rest of the structure, action, and effect are similar as in the first embodiment.

Third Embodiment

Figure 9:
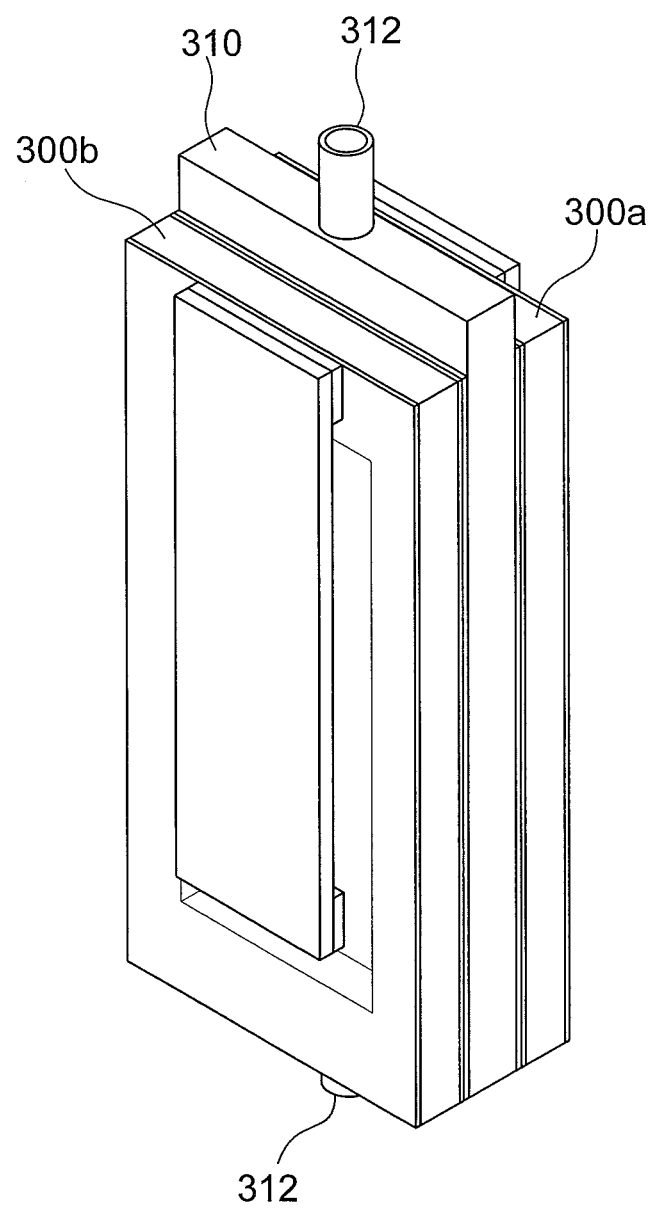
FIG. 9 is a perspective view showing a structure of a micro pump according to a third embodiment.
Figure 10:
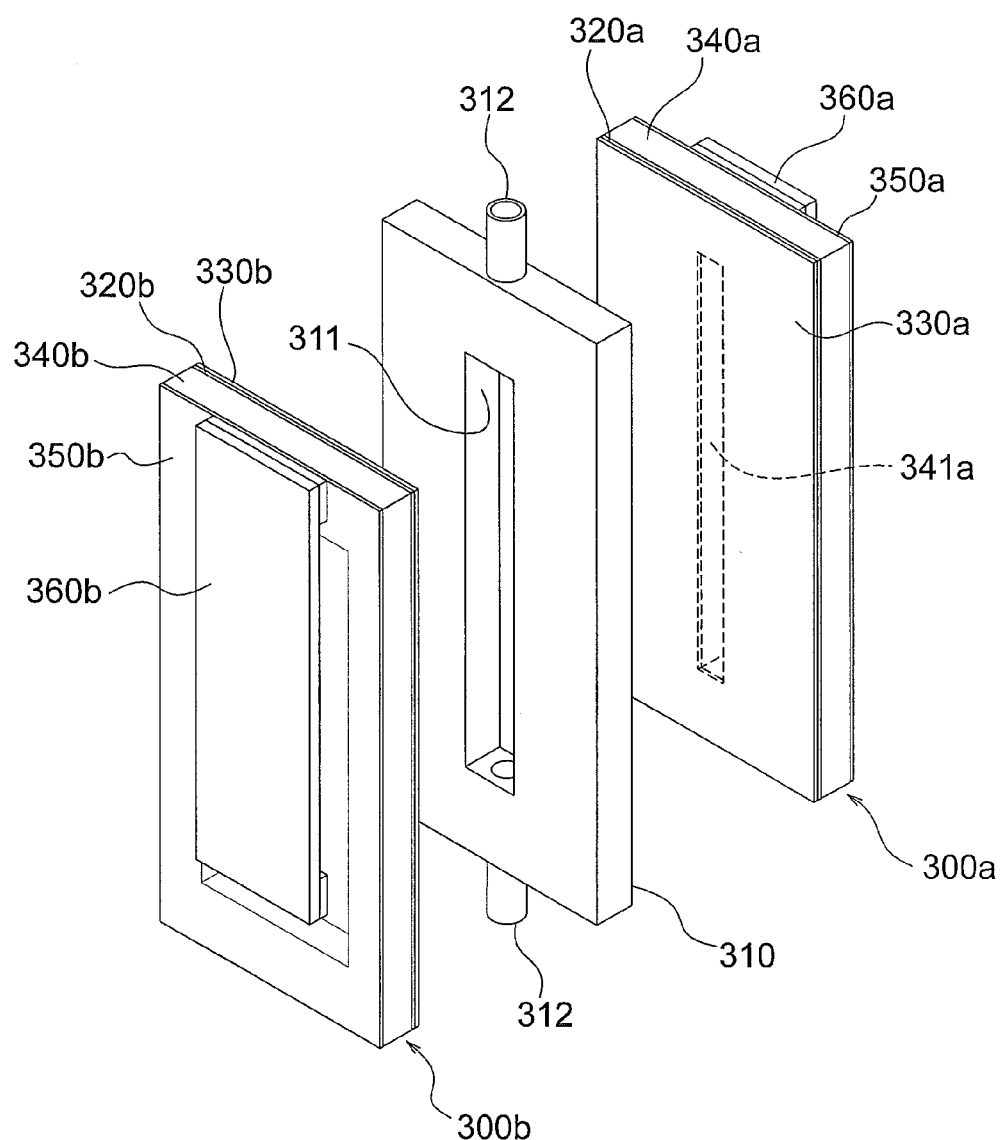
FIG. 10 is a perspective view showing the micro pump according to the third embodiment, to be partly exploded.
Figure 11:
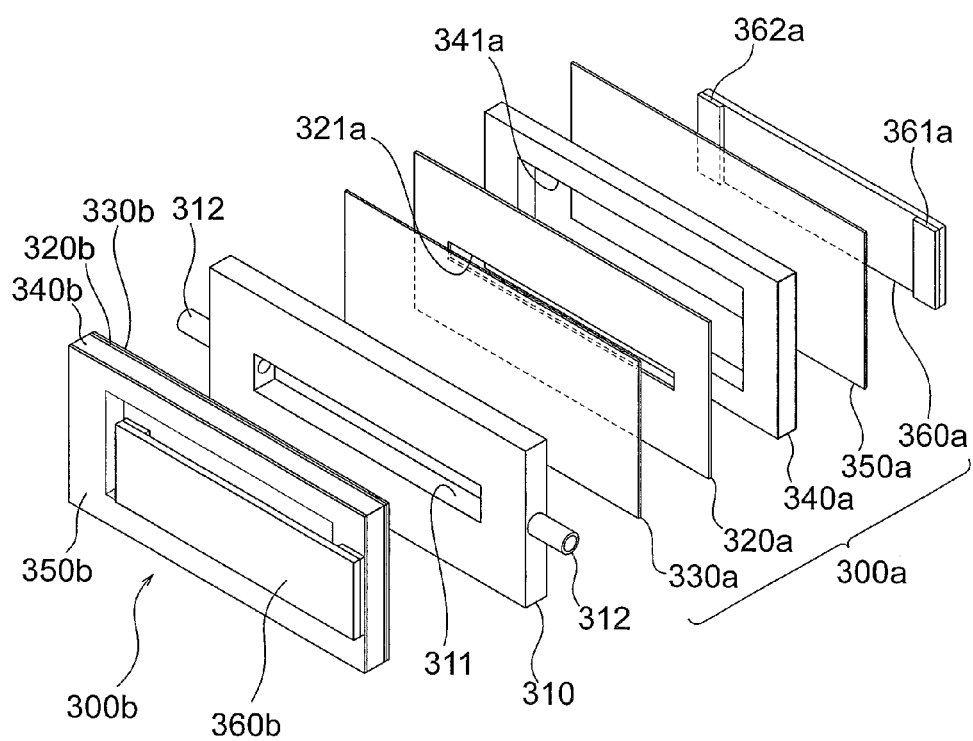
FIG. 11 is a perspective view showing FIG. 10 further exploded.

FIG. 9 is a perspective view showing a structure of a micro pump 300 according to a third embodiment. FIG. 10 is a perspective view showing the micro pump 300 to be partly exploded. FIG. 11 is a perspective view showing FIG. 10 further exploded.

In the micro pump 100 according to the first embodiment, the fluid has been moved by providing a mechanism (vibration exciter unit) which generates a progressive wave, on one side surface of the PDMS fluid channel 110 provided with the channel 111. Whereas, in the micro pump 300 according to the third embodiment, for further augmenting a flow inside a channel 311, a first pump 300a (vibration exciter unit) and a second pump 300b (vibration exciter unit) are provided on two face-to-face side surfaces respectively, of a PDMS fluid channel 310 which is provided with a channel 311. In the third embodiment, although the pumps are provided to only two surfaces of the PDMS fluid channel 310, the pumps may be disposed similarly on the other surfaces as well.

The first pump 300a and the second pump 300b have a substantially same structure, and first PDMS films 330a and 330b are disposed to be directed mutually, on two face-to-face surfaces respectively, of the PDMS fluid channel 310. Consequently, the first pump 300a and the second pump 300b are disposed symmetrically about the PDMS fluid channel 310. Accordingly, the channel 311 is formed by being surrounded by an inner wall of the PDMS fluid channel 310, and the first PDMS films 330a and 330b, and communicates with a connecting port 312 which is extended to an exterior. The liquid F1 to be transported is accommodated inside the channel 311.

The first pump 300a has a structure in which, the first PDMS film 330a as the first flexible thin film, a titanium cover 320a which has an opening portion 321a at a position corresponding to the channel 311, a silicon substrate 340a in which, a chamber 341a is formed at a position corresponding to the opening portion 321a in the chamber 320, the second PDMS film 350a as the second flexible thin film, and an actuator 360a are stacked in order from the PDMS fluid channel 310 side.

The second pump 300b has a structure in which, the first PDMS film 330b as the first flexible thin film, a titanium cover 320b, a silicon substrate 340b, a second PDMS film 350b as the second flexible thin film, and an actuator 360b are stacked in order from the PDMS fluid channel 310 side. Since the first PDMS film 330b, the titanium cover 320b, the silicon substrate 340b, the second PDMS film 350b, and the actuator 360b correspond to the first PDMS film 330, the titanium cover 320a, the silicon substrate 340a, the second PDMS film 350a, and the actuator 360a of the first pump 300 respectively, the description in detail thereof is omitted.

The chamber 341a is cut through the silicon substrate 340a in a direction of thickness thereof, and apart from an inner wall of the silicon substrate 340a, the PDMS fluid channel 310 side is covered by the first PDMS film 330a via the titanium cover 320a, and a side opposite to the PDMS fluid channel 310 side is covered by the second PDMS film 350a. The incompressible fluid F2 is filled in the chamber 341a.

A contact-pressure member 362a which is displaced by the actuator 360a of piezoelectric type which is curved is disposed to be in contact on the second PDMS film 350a. The contact-pressure member 362a is fixed to one end portion of the actuator 360a in the form of a long plate, as well as is disposed at a position on one end portion side in a longitudinal direction of the chamber 341a, corresponding to the channel 311. Moreover, the other end portion of the actuator 360a is fixed to the second PDMS film 350a via fixing portion 361a.

In the first pump 300a, the actuator 360a and the contact-pressure member 362a form the vibration exciter mechanism. Moreover, the first PDMS film 330a, the titanium cover 320a, the silicon substrate 340a, the second PDMS film 350a, and the incompressible fluid F2 inside the chamber 341a constitutes the vibration exciter unit.

By making the contact-pressure member 362a vibrate by supplying an electric power to the actuator 360a of piezoelectric type, an end portion of the second PDMS film 350a is excited by vibration in the out-of-plane direction (direction in which, the first pump 300a and the second pump 300b are stacked). Due to the excitation by vibration, a progressive wave in a direction in which the channel 311 is extended is generated in the second PDMS film 350a. Since the chamber 341a is filled with the incompressible fluid F2, due to the progressive wave generated in the second PDMS film 350a, a corresponding progressive wave is generated in the first PDMS film 330a via the titanium cover 320a.

Moreover, both the opening portion 321a formed in the titanium cover 320a and the chamber 341a formed in the silicon substrate 340a are through holes having a rectangular shape which is longer in the direction of the channel 311. The opening portion 321a has a width narrower than the chamber 341a. Since a stiffness of the titanium cover 320a is higher than a stiffness of the first PDMS film 330a, a displacement of the first PDMS film 330a is suppressed by a portion covered by the titanium cover 320a, and the displacement of the first PDMS film 330a occurs in a range corresponding to the opening portion 321a of the titanium cover 320a. In other words, from a view point of the range of displacement, practically, the range in which the displacement occurs in the first PDMS film 330a becomes smaller than a range in which, the displacement occurs in the second PDMS film 350a.

In such manner, a displaceable range by the titanium cover 320a for the first PDMS film 330a on the PDMS fluid channel 310 side is formed to be practically smaller as compared to a displaceable range for the second PDMS film 350a. Therefore, the displacement in the out-of-plane direction of the first PDMS film 330a on the PDMS fluid channel 310 side is restricted to the range corresponding to the opening portion 321a, and becomes larger than the displacement of the second PDMS film 350a. In other words, by making the opening portion 321a smaller than the chamber 341a, an effect of augmentation of the displacement in the out-of-plane direction in (for) the first PDMS film 330a is achieved. Consequently, it is possible to transport a liquid by a single actuator for vibration excitation and also a large flow of liquid to be transported is achieved by a small displacement of the actuator for vibration excitation.

Furthermore, unlike in the micro pump 100 according to the first embodiment, two pumps namely the first pump 300a and the second pump 300b are disposed on two surfaces respectively of the channel 311. Therefore, a larger flow as compared to by the micro pump 100 according to the first embodiment is achieved. Consequently, for an application in which, constraints on the overall size are comparatively loose, the micro pump according to the third embodiment is favorable.

The rest of the structure, action, and effect are similar as in the first embodiment.

INDUSTRIAL APPLICABILITY

As it has been described above, the pump unit according to the present invention is suitable for an endoscope apparatus for which, a pump having a small size and a large flow has been sought.

REFERENCE SIGNS LIST 100 micro pump (pump unit)
110 PDMS fluid channel
111 channel
112 tube
113 water-cooling tube
120 titanium cover
121 opening portion
130 first PDMS film
140 silicon substrate
141 chamber
150 second PDMS film
160 actuator
161 contact-pressure member
170 casing
180 metallic member
200 micro pump (pump unit)
230 first PDMS film
240 silicon substrate
241 chamber
250 second PDMS film
300 micro pump (pump unit)
300a first pump
300b second pump
310 PDMS fluid channel
311 channel
312 connecting port
320a titanium cover
321a opening portion
330a first PDMS film
330b first PDMS film
340a silicon substrate
340b silicon substrate
341a chamber
350a second PDMS film
350b second PDMS film
360a actuator
360b actuator
361a fixing portion
362a contact-pressure member

The invention claimed is:

1. A pump comprising:
a pump body having a channel for the flow of a fluid, the channel being open on at least one surface of the pump body;
a primary flexible film disposed on the at least one surface of the pump body to enclose the channel such that a portion of a surface area of the primary flexible film is free to deform into the channel;
a substrate disposed on the primary flexible film and having a chamber open on first and second surfaces, the primary flexible film enclosing the chamber on the first surface of the substrate;
a secondary flexible film disposed on the substrate, the secondary flexible film enclosing the chamber on the second surface of the substrate such that a portion of a surface area of the secondary flexible film is free to deform into the chamber;
a non-compressive fluid disposed in the chamber; and
a generator having a single actuator, the single actuator being operatively connected to the secondary flexible film to generate a primary progressive wave in the secondary flexible film, the primary progressive wave being transferred from the secondary flexible film by the non-compressible fluid to generate a resultant progressive wave in the primary flexible film to pump the fluid through the channel.

2. The pump of claim 1, wherein the portion of the surface area of the secondary flexible film being larger than the portion of the surface area of the primary flexible film to amplify the resultant progressive wave as compared to the primary progressive wave.

3. The pump of claim 1, further comprising a plate member having an opening, the opening varying the portion of the surface area of the primary flexible film that is free to deform into the channel.

4. The pump of claim 3, wherein the plate member being disposed between the primary flexible film and the pump body.

5. The pump of claim 3, wherein the size of the opening in the plate member decreases the portion of the surface area of the primary flexible film that is free to deform into the channel.

6. The pump of claim 1, wherein the first and second surfaces of the substrate are formed in a plane and the chamber is rectangular in cross-section in the plane.

7. The pump of claim 6, wherein the surface of the pump body is formed in the plane and the channel is rectangular in cross-section in the plane.

8. The pump of claim 7, wherein the primary and secondary flexible films are formed in the plane and the single actuator generates the primary progressive wave transverse to the plane.

9. The pump of claim 1, wherein the single actuator comprises a piezoelectric actuator.

10. The pump of claim 1, wherein a cross-section of the chamber is constant between the first and second surfaces.

11. The pump of claim 1, wherein a cross-section of the chamber varies between the first and second surfaces.

12. A pump comprising:
a pump body having a channel for the flow of a fluid, the channel being open on two surfaces of the pump body;
a primary flexible film disposed on each of the two surfaces of the pump body to enclose the channel such that a portion of a surface area of each of the primary flexible films is free to deform into the channel;
a substrate disposed on each of the primary flexible films, each substrate having a chamber open on first and second surfaces, each of the primary flexible films enclosing the chamber on the first surface of each of the substrates;
a secondary flexible film disposed on each of the substrates, each of the secondary flexible films enclosing the chamber on each second surface of each of the substrates such that a portion of a surface area of each of the secondary flexible films is free to deform into the respective chamber;
a non-compressive fluid disposed in each of the chambers; and
a generator operatively connected to each of the secondary flexible films to generate a primary progressive wave in each of the secondary flexible films, each primary progressive wave being transferred from each of the secondary flexible films by the respective non-compressible fluid to generate a resultant progressive wave in each of the primary flexible films to pump the fluid through the channel.

13. An endoscope comprising:
a heat source;
a part which is heated by the heat source; and
a cooling mechanism operatively connected to the part to lower a temperature of the part, the cooling mechanism comprising:
a circulation channel having a cooling fluid; and
a pump disposed within the circulation channel to pump the cooling fluid through the circulation channel, the pump comprising:
a pump body having a channel in communication with the circulation channel, the channel being open on at least one surface of the pump body;
a primary flexible film disposed on the at least one surface of the pump body to enclose the channel such that a portion of a surface area of the primary flexible film is free to deform into the channel;
a substrate disposed on the primary flexible film and having a chamber open on first and second surfaces, the primary flexible film enclosing the chamber on the first surface of the substrate;
a secondary flexible film disposed on the substrate, the secondary flexible film enclosing the chamber on the second surface of the substrate such that a portion of a surface area of the secondary flexible film is free to deform into the chamber, the portion of the surface area of the secondary flexible film being larger than the portion of the surface area of the primary flexible film;
a non-compressive fluid disposed in the chamber; and
a generator having a single actuator, the single actuator being operatively connected to the secondary flexible film to generate a primary progressive wave in the secondary flexible film, the primary progressive wave being transferred from the secondary flexible film by the non-compressible fluid to generate an amplified resultant progressive wave in the primary flexible film to pump the fluid through the channel and the circulation channel.

14. The endoscope of claim 13, wherein the heat source is an electronic component disposed at a front-end portion of the endoscope.

15. The endoscope of claim 14, wherein the part is a metallic part upon which the electronic component is mounted.

* * * * *